United States Patent [19]

Lewis et al.

[11] Patent Number: 4,889,838
[45] Date of Patent: Dec. 26, 1989

[54] REDISTRIBUTION OF ORGANOHALOSILANES UTILIZING HEAT TREATED CRYSTALLINE ALUMINA CATALYSTS

[75] Inventors: Kenrick M. Lewis, New York, N.Y.; Ching-Feng Chang, Strongsville, Ohio

[73] Assignee: Union Carbide Corporation and Plastics Company Inc., Danbury, Conn.

[21] Appl. No.: 564,374

[22] Filed: Dec. 22, 1983

[51] Int. Cl.$^4$ .......................... B01J 38/60; C07F 7/12
[52] U.S. Cl. ..................................... 502/27; 423/342; 556/469
[58] Field of Search ........................ 423/342; 556/469; 502/64, 355, 27.416

[56] References Cited

U.S. PATENT DOCUMENTS

| | | |
|---|---|---|
| 2,380,995 | 8/1945 | Rockow . |
| 2,590,937 | 4/1952 | Clark . |
| 2,647,136 | 7/1953 | Sauer . |
| 2,647,912 | 8/1953 | Barry et al. . |
| 2,786,861 | 3/1957 | McEntee . |
| 3,065,253 | 11/1962 | Merritt . |
| 3,147,071 | 9/1964 | Jenkner ............................. 423/342 |
| 3,207,699 | 9/1965 | Harding et al. . |
| 3,346,349 | 10/1967 | Harding et al. . |
| 3,362,977 | 1/1968 | Berger ................................. 556/469 |
| 3,384,652 | 5/1968 | Hamilton . |
| 3,655,710 | 4/1972 | Bazouin et al. . |
| 3,730,540 | 1/1956 | Sauer . |
| 3,793,357 | 2/1979 | McEntee . |
| 3,980,686 | 9/1976 | Lefort et al. . |
| 4,155,927 | 5/1979 | Straussberger et al. . |
| 4,158,010 | 6/1979 | Graf et al. . |
| 4,297,500 | 10/1981 | Finke et al. . |
| 4,404,417 | 9/1983 | Adams et al. ....................... 502/355 |

FOREIGN PATENT DOCUMENTS

| | | |
|---|---|---|
| 1822 | 3/1957 | Japan . |
| 23172 | of 1961 | Japan . |
| 38-9272 | 6/1963 | Japan ................................. 556/469 |
| 3026 | of 1964 | Japan . |

OTHER PUBLICATIONS

K. Tanabe, Solid Acid and Bases, Academic Press, N.Y. 1970, pp. 123-133.

Morterra et al., Journal of Catalysis, vol. 51, pp. 299-313 (1978).

Morterra et al., Journal of Catalysis, vol. 54, pp. 348-364 (1978).

MacZura et al., Kirk-Omther Encylopedia of Chemical Technology, 3rd Ed., vol. 2, pp. 225-233, John Wiely & Sons, N.Y. 1978.

K. Weters and G. Bell, "Oxides and Hydroxides of Aluminum Technical Paper 19", Alcoa.

B. Linsen, "Physical and Chemical Aspects of Adsorbents and Catalysts", Academic Press, London, 1970, (Chapter 4-Lippens et al.).

Primary Examiner—Robert L. Stoll
Assistant Examiner—Jeffrey Edwin Russel
Attorney, Agent, or Firm—Paul W. Leuzzi

[57] ABSTRACT

A method of redistributing a mixture of organohalosianes, particularly methylchlorosilanes by contacting said mixture with a heat treated crystalline gamma alumina or eta alumina catalyst.

3 Claims, 2 Drawing Sheets

REDISTRIBUTION OF ORGANOHALOSILANES UTILIZING HEAT TREATED CRYSTALLINE ALUMINA CATALYSTS

TECHNICAL FIELD

This invention relates to a method for the redistribution of organohalosilanes utilizing heat treated crystalline gamma alumina or eta alumina catalysts. More particularly, this invention relates to the production of trimethylchlorosilane by the redistribution of mixtures of other methylchlorosilanes.

BACKGROUND ART

The preparation of methylchlorosilanes by direct synthesis (Rochow Synthesis See U.S. Pat. No. 2,380,995), results in the unavoidable formation of a considerable proportion of low-boiling products with a boiling point of less than 40° C. (760 mmHg.). Said low-boiling products include for example, tetramethylsilane, dimethylchlorosilane, methyldichlorosilane, methylchlorosilane, trichlorosilane, methylchloride, hydrocarbons, etc. A method of converting the above-mentioned low-boiling product mixture into compounds (especially trimethylchlorosilane) more useful in the silicones industry is needed.

Many redistribution and alkylation methods are known in the art for the preparation of organohalosilanes from other silanes utilizing aluminum catalysts and reactants, and other materials. Thus, the preparation of organohalosilanes from other silanes has been achieved using a wide variety of catalysts, co-catalysts and reactants such as silica alumina, zeolites, methyl chloride metallic aluminum, hydrogen chloride, aluminum trichloride, methylaluminum halides, etc. Generally, of the Lewis acid activated catalysts, aluminum trichloride was the most widely used for these types of reactions. The utilization of aluminum trichloride and organoaluminum compounds as reagents and/or catalysts in these processes however, was fraught with numerous difficulties.

A redistribution reaction is a rearrangement of at least two different substituents which are attached to a silicon atom or atoms Two or more silanes having differing numbers of substituents such as $CH_3$ or $Cl$, for example, redistribute when said substituents exchange silicon sites. The resulting product or products still have a total of four substituents or atoms attached to the silicon atom, but in ratios different from that of the starting compounds. A typical redistribution reaction can be illustrated by the following:

$(CH_3)_4Si + (CH_3)_2SiCl_2 \rightleftharpoons 2(CH_3)_3SiCl$

A disproportionation reaction is a type of redistribution reaction that occurs when a single silicon compound yields two or more dissimilar silicon compounds having substituents (i.e. $CH_3$ and $Cl$) in differing proportions from that of the initial starting compound A disproportionation reaction can be illustrated by the following:

$2(CH_3)_2SiCl_2 \rightleftharpoons CH_3SiCl_3 + (CH_3)_3SiCl$

The use of organoaluminum compounds in general results in pyrophoric, potentially explosive, and readily hydrolyzable organoaluminum by-products which must be disposed of via lixiviation with water or alkali. This can be extremely hazardous because of the attendant hydrolysis of methylchlorosilanes to yield hydrogen chloride. Aluminum trichloride has appreciable solubility in methylchlorosilane mixtures which can produce separation and purification problems. Plugging problems in transport lines and distillation columns are usually concomitant with its use. Additionally, the use of aluminum trichloride involves long contact times ranging anywhere from two to twenty-four hours.

U.S. Pat. Nos. 2,647,136, 2,786,861 and 3,793,357 all employ the use of an aluminum trichloride catalyst in the preparation of an alkylhalosilane by redistribution. The latter two patents also employ the use of an $\equiv$SiH compound as the promoter or co-catalyst thus permitting the use of lower reaction temperatures. All of these patents, however, disclose processes operated under autogenous pressure and at temperatures between 150–400° C. for periods of two to twenty-four hours. Other patents which utilize an aluminum trichloride catalyst with or without a co-catalyst include U.S. Pat. Nos. 2,730,540, 3,655,710 and 3,980,686. It should be noted, however, that not all Lewis-acid catalysts such as "boron trichloride, zinc chloride, iron chloride, copper chloride, etc." exert a "perceptible effect" on the course of these reactions. (U.S. Pat. No. 2,647,136, Column 3, Lines 69–75). Japanese Pat. 3026 (1964) discloses the preparation of phenylmethyldichlorosilane from phenyltrichlorosilane and tetramethylsilane utilizing an activated alumina catalyst at 240° C. for 10 hours in an autoclave. Japanese Pat. 1822 (1957) discloses the preparation of methyltrichlorosilane from trimethylchlorosilane and silicon tetrachloride utilizing an activated alumina catalyst at 280° C. for 4 hours. Contrastingly, Japanese Pat. 23,172 (1961) shows that $CH_3SiHCl_2$ is obtained by heating $(CH_3)_3SiCl$ and $HSiCl_3$ in the presence of alumina at 200°–400° C. under autogenous conditions for up to 10 hours. Though all these patents disclose the use of activated alumina catalysts, the reactions involved require significantly longer reaction times (contact time) typically, of four hours or longer.

The use of methylaluminum sesquichloride to methylate methyl-trichlorosilane is disclosed in U.S. Pat. No. 3,065.253. Here SiH compounds. e.g. methyldichlorosilane, is advantageously used to shorten the reaction time from 20 hours to 2 hours.

U.S. Pat. No. 4,155,927 discloses a process for preparing trimethylchlorosilane by reacting methyldichlorosilane with methyl chloride and metallic aluminum. Methylchloride reacts with aluminum to form methylaluminum sesguichloride. The organoaluminum compound methylaluminum sesquichloride is the methylating agent which reacts with methyldichlorosilane to form aluminum trichloride and trimethylchlorosilane. This reaction is a methylation reaction not a redistribution reaction. This process is not catalytic. Furthermore the production of $AlCl_3$ results in hazardous waste disposal problems as previously mentioned.

U.S. Pat. No. 4,297,500 discloses a process for synthesizing trimethylchlorosilane from the low-boiling ($<40°$ C.) fraction of the Rochow direct synthesis (U.S. Pat. No. 2,380,995) by hydrochlorination of this fraction in the presence of catalytic amounts of $AlCl_3$. The amount of HCl employed must be at least equal to the molar amount of tetramethylsilane in the low-boiling fraction. $AlCl_3$ is disclosed in this patent as a catalyst for the hydrochlorination reaction rather than redistribution.

U.S. Pat. No. 4,158,010 discloses an improved redistribution process for preparing organosilanes by reacting a mixture of alkylhalosilanes with silanes containing an Si-H bond in the presence of organoaluminum compounds and hydrogen halides. The various forms or organoaluminum compounds utilized include: ethylaluminum dichloride, trimethylaluminum, methylaluminum sesquichloride, etc. This patent teaches (see Example 4) the synthesis of trimethylchlorosilane from the low-boiling fraction of the Rochow direct synthesis and added methyltrichlorosilane by heating the reaction mixture at reflux for 6 hours in the presence of methylaluminum sesquichloride and hydrogen chloride. In effect, this method combines hydrochlorination and methylation with redistribution at long contact times.

The process of U.S. Pat. Nos. 3,065,253; 4,155 927; 4,297 500 and 4 158,010 are all hampered by the hazardous handling and disposal problems associated with the use of $AlCl_3$, organoaluminum halides and gaseous HCl.

U.S. Pat. No. 3,384,652 discloses a method for the production of chlorosilanes and organic substituted chlorosilanes by disporportionation and condensation reactions of mixtures of organochlorosilanes in the presence of crystalline aluminosilicate catalysts (zeolites). These "aluminosilicate materials may also be converted to the H or acid form in which hydrogen ions occupy the cation ion sites" (Column 4, Lines 41-43). In general, "the H form is more stable in materials having $SiO_2/Al_2O_3$ of 3.5 or higher" (Column 4, Lines 45-47). Thus method utilizes zeolites having Bronsted acid sites. Moreover, as in the case of previous processes this reaction requires long contact times.

U.S. Pat. No. 3,207,699 relates primarily to the preparation of catalysts by chemically attaching a restricted quantity of alkylsilyl groups to the internal surface of an acidic refractory oxide of one or more metals (e.g., silica-alumina) at an elevated temperature, cooling the treated acidic refractory oxide in an atmosphere containing no oxygen, whereby the catalytic properties of the acidic cracking catalyst are significantly modified without completely destroying the acidity of the catalyst. Prior to attaching the alkysilyl groups, the refractory oxide is dried at elevated temperatures in order to prevent the reaction of the silane with water because the latter reaction interferes with the desired reaction of the silane with the refractory oxide. This patent discloses that the refractory oxide contains significant cracking activity both before and after treatment with the silane. The treated catalysts so produced are disclosed as being useful as redistribution (specifically disproportionation) catalysts for trimethylsilane. U.S. Pat. No. 3,346,349 relates primarily to the use of treated aluminaceous catalysts, including those of U.S. Pat. No. 3,207,699, as redistribution (specifically disproportionation) catalysts for various silanes. In U.S. Pat. No. 3,346,349 both the class of silanes that can be used to treat the catalysts and the class of silanes that can be redistributed by the treated catalysts are expanded beyond the disclosure of U.S. Pat. No. 3,207,699. U.S. Pat. No. 3,346,349 contains a disclosure similar to the disclosure of U.S. Pat. No. 3,207,699 with respect to the drying of the untreated catalyst and to the method of treatment of the dried catalyst with the silane. U.S. Pat. No. 3,346,349 makes no reference to the cracking activity either of the untreated catalyst or of the treated catalyst. However, in view of the similar treating conditions, it would appear that the treated catalysts of both patents should have similar properties. As is shown in K. Tanabe, Solid Acids and Bases, Academic Press. N.Y. 1970. pp. 123-133, cracking activity in silica-alumina catalysts is associated with the presence of Bronsted acid sites on the catalyst. Hence, accepting the teachings of U.S. Pat. Nos. 3,207,699 and 3 346,349 at face value, it appears they relate to redistribution catalysts with Bronsted acid sites rather than Lewis acid sites. However, it is possible that the silanes reacted with all the Bronsted acid sites on the surface of the silica and alumina in the treatment process of these patents and so the "catalysts" actually become non-acidic during treatment. In view of the high redistribution temperatures actually used in the Examples (e.g. 510° C.), the redistribution reactions reported in these patents may simply have been thermally-induced redistribution reactions as distinguished from catalytically induced redistribution reactions. The possible lack of catalytic activity of the treated oxides of these references (despite the disclosure in U.S. Pat. No. 3 207,699 that the treated catalysts retain significant cracking activity) is also consistent with the fact that the examples of the patents make no reference to any cracking reaction after the initial treatment of the silane. Japanese Pat. 23,172/1961, however, illustrates that methyldiohlorosilane is obtained by heating trimethylchlorosilane and trichlorosilane in the presence of an alumina catalyst at 200-400° C. and under autogenous conditions for up to 10 hours. Longer residence times and/or higher temperatures promote the formation of silane, a known pyrophoric compound.

It is an object of the present invention to provide a method for the redistribution and/or disproportionation of mixtures of organohalosilanes utilizing a heat treated crystalline alumina catalyst.

More specifically, it is an object of the present invention to prepare trimethylchlorosilane from mixtures of other methylchlorosilanes, especially those derived from the lower-boiling fraction of the Rochow synthesis utilizing a heat treated crystalline alumina catalyst It is an object of the present invention to effect such redistribution and/or disproportionation reaction without the use of aluminum trichloride or other organoaluminum compounds.

It is an object of the present invention to effect such redistribution and/or disporportionation reaction utilizing short contact times.

It is a further objective of the present invention to effect regeneration and reuse of said heat treated crystalline alumina catalyst.

SUMMARY OF THE INVENTION

This and other objects of the invention which will be apparent to those skilled in the art are achieved by the present invention which relates to: a method for redistributing the halogen atom of a halosilane and at least one member selected from the group consisting of the hydrocarbyl group of a hydrocarbylsilane and the hydrogen atom of a hydrosilane which method comprises contacting a mixture of the halosilane, hydrocarbylsilane and/or the hydrosilane, with a heat treated crystalline gamma alumina or eta alumina catalyst at 200° C.-450° C. for a maximum contact time of ten minutes said heat treated catalyst having been activated at 400° C.-500° C.

In a preferred embodiment, this invention relates to: a method of catalytically redistributing a mixture of compounds having the formulas:

$R_nSiX_{4-n}$, and $R_mSiHX_{3-m}$ wherein R is an alkyl group having from 1 to 55 carbon atoms, or an phenyl group, X is a halogen. $n \leq 4$, and $m \leq 3$, which method comprises contacting the mixture of compounds with a heat treated crystalline gamma alumina or eta alumina catalyst at 200° C.–450° C. for a maximum contact time of ten minutes, said heat treated catalyst having been activated at 400° C.–500° C.

Another preferred embodiment of the present invention relates to: a method of catalytically redistributing the halogen, the hydrogen, the alkyl groups and/or phenyl groups of a single silane represented by the formula:

$$R_nSiX_{4-n}$$

wherein R is hydrogen, an phenyl group, or an alkyl group containing from 1 to 5 carbon atoms, X is a halogen and n has a value from 1 to 3 inclusive, which method comprises contacting the silane with a heat treated crystalline gamma alumina or eta alumina catalyst at 200° C.–450° C. for a maximum contact time of ten minutes, said heat treated catalysts having been activated at 400° C.–500° C.

DETAILED DESCRIPTION OF DRAWINGS

Figure 1:
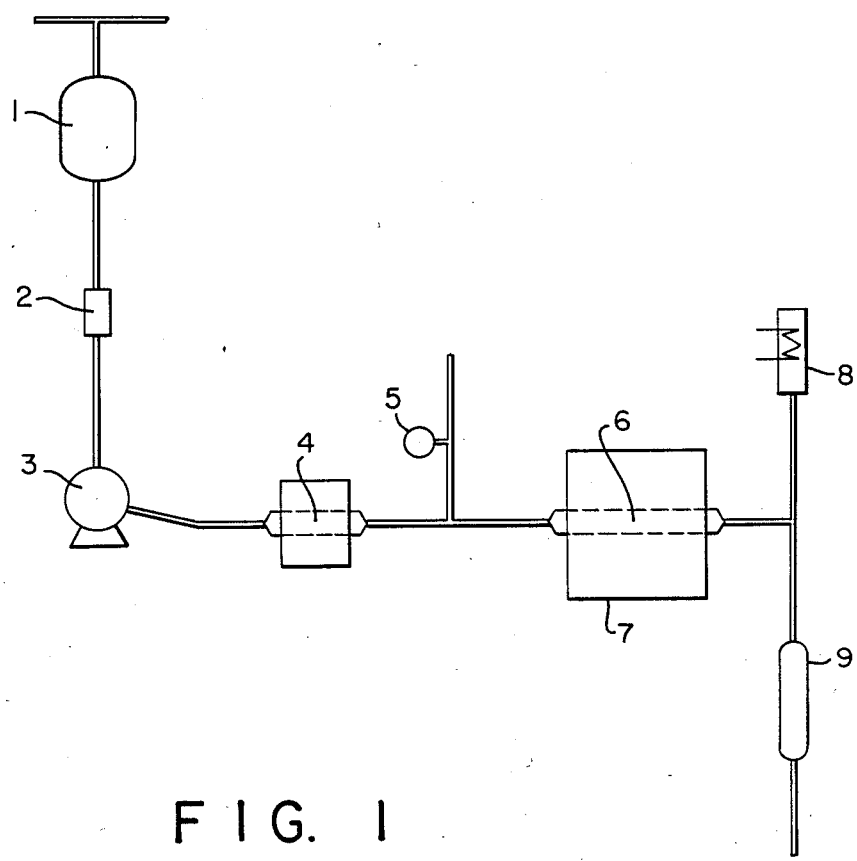
FIG. 1 is a schematic drawing depicting apparatus suitable for use in carrying out the redistribution reaction of the present invention.

The embodiments of the present invention are best understood by referring to FIG. 1. The silane reactants are stored in the vessel 1 and passed through the sintered stainless steel filter 2 to the calibrated pump 3. Liquid from the pump is flash evaporated at 300°–400° C. in the vaporizer 4. The inlet pressure is recorded by the pressure indicator 5. The vaporized reactants are admitted to the reactor 6 that is made from Hastelloy B pipe which is equipped with reducing fittings for reactant introduction and product outlet and which contains a gamma alumina catalyst bed. Quartz wool is placed at both ends of the pipe to keep the γ-alumina bed in place in the heated zone. The reactor is heated in a tube furnace 7. At the reactor outlet the gaseous silane product mixture is led to a condenser 8 and cooled by a suitable refrigerant, i.e., dry ice—isopropanol. The liquid silane product collected in the receiver 9 is subsequently analyzed and distilled. The practice of this invention is not in any way limited to the apparatus depicted herein. The valves and other minor fittings which would be obvious to those skilled in the art have been omitted.

Figure 2:
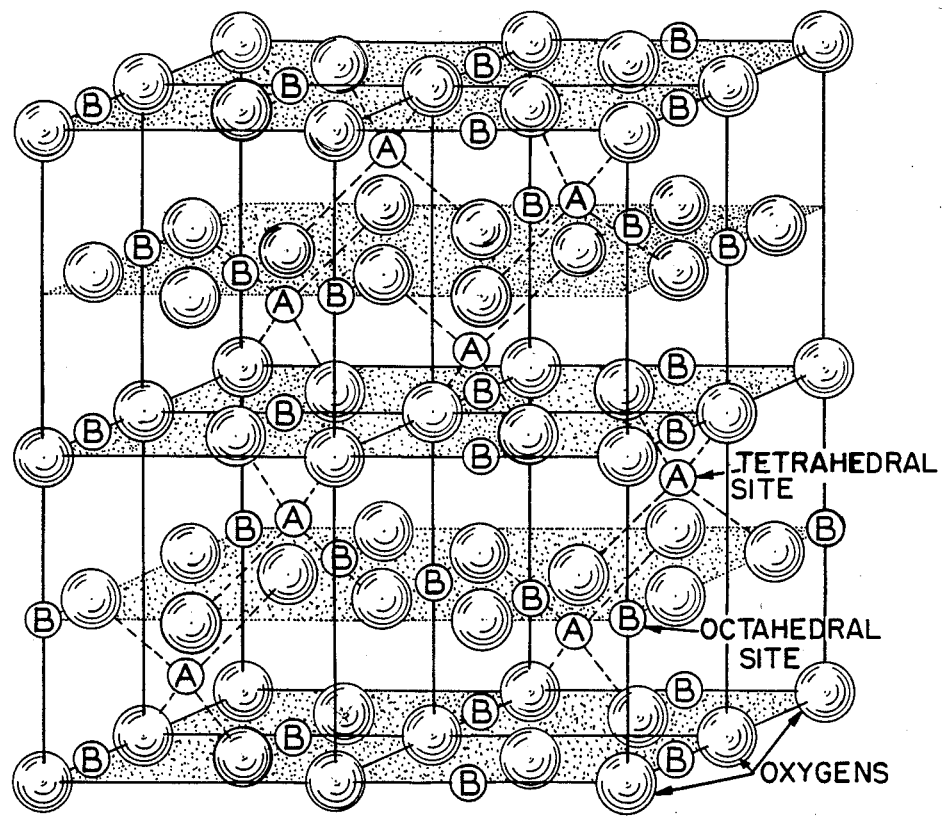
FIG. 2 is an illustration of a spinal structure which is arranged in cubic close packing. Bloss, F. Donald, "Crystallography and Crystal Chemistry. Pg. 255, Publ.: Holt, Rhinehart and Winston, NY 1971)

A better understanding of FIG. 2 will be achieved when said drawing is read in conjunction with the detailed description of the invention.

DETAILED DESCRIPTION OF THE INVENTION

The present invention is a method of redistributing the halogen of a halosilane and at least one member selected from the group consisting of the hydrocarbyl group of a hydrocarbylsilane and the hydrogen atom of a hydrosilane which method comprises contacting a mixture of the halosilane. hydrocarbylsilane and/or the hydrosilane with a heat treated crystalline gamma alumina or eta alumina catalyst at 200° C.–450° C. for a maximum contact time of ten minutes, said heat treated catalyst having been activated at 400° C.–500° C.

A halosilane is defined as any silane containing a halogen atom directly bonded to the silicon atom. A hydrocarbylsilane is defined as any silane containing an alkyl group having from one to five carbon atoms or an phenyl group which is directly bonded to the silicon atom. A hydrosilane is defined as any silane containing a hydrogen atom which is directly bonded to the silicon atom.

In a preferred embodiment, the present invention is a method of catalytically redistributing or disproportionating a mixture of compounds having the formulas: $R_nSiX_{4-n}$ and $R_mSiHX_{3-m}$, wherein R is an alkyl group having from one to five carbon atoms, or an phenyl group, X is a halogen, $n \leq 4$, and $m \leq 3$, which method comprises contacting the mixture of compounds with a heat treated crystalline gamma alumina or eta alumina catalyst at 200° C.–450° C. for a maximum contact time of ten minutes, said heat treated catalyst having been activated at 400° C.–500° C. Another preferred embodiment of the present invention is a method of catalytically redistributing the halogen, the hydrogen, the alkyl groups and/or aryl groups of a single silane represented by the formula:

$$R_nSiX_{4-n}$$

wherein R is hydrogen, an phenyl group or an alkyl group containing from 1 to 5 carbon atoms, X is a halogen, and n has a Value from 1 to 3 inclusive, which method comprises contacting the silane with a heat treated crystalline gamma alumina or eta alumina catalyst at 200° C.–450° C. for a maximum contact time of ten minutes said heat treated catalysts having been activated at 400° C.–500° C. Illustrative of the compounds represented by R are the following:

| | |
|---|---|
| $CH_3SiCl_3$ | $(C_3H_7)SiCl_3$ |
| $(CH_3)_2SiCl_2$ | $(C_4H_9)_2SiCl_2$ |
| $C_2H_5SiCl_3$ | $ArSiCl_3$ |
| $(C_2H_5)_2SiCl_2$ | $Ar_2SiBr_2$ |
| $(C_2H_5)_3SiCl$ | $Ar_3SiCl$ |
| $(CH_3)_4Si$ | $(C_6H_5)_4Si$ |
| $(C_2H_5)_4Si$ | $(C_3H_7)_4Si$ |

Illustrative of the compounds represented by $R_mSiHX_{3-m}$ are the following:

| | |
|---|---|
| $(CH_3)_3SiH$ | $(C_3H_7)_2SiHCl$ |
| $(CH_3)_2SiHBr$ | $ArSiHBr_2$ |
| $CH_3SiHCl_2$ | $Ar_2SiHBr$ |
| $(C_2H_5)_2SiHCl$ | |

In order to more fully understand the origin of Lewis acid sites in gamma alumina (γ-$Al_2O_3$) and eta alumina (η-$Al_2O_3$), their structures must be considered. A Bronsted acid is a proton donor (H+). A Lewis acid is an electron pair acceptor (electron deficiency).

The crystal structure of η- and γ-$Al_2O_3$ is similar to that of spinel $MgAl_2O_4$ (Refer to FIG. 2). In the structure of a spinel, all the oxygen anions are equivalent and are arranged in cubic close packing. The $Mg^{2+}$ ions occupy the tetrahedral positions (A) in this cubic structure and are surrounded by four oxide anions (o). The Al³⁺ ions occupy the octahedral positions (B) wherein they are in turn surrounded by six oxide anions. In the spinel structure the ratio of metal cations to oxide anions is 3:4 and in the activated aluminas. This ratio is 2:3. A fraction of the cation sites, as is clear from FIG. 2 remain vacant and the aluminas, as a result, show varying degrees of structural disorder. $\eta$-Al$_2$O$_3$ relatively more Al³⁺ ions in tetrahedral positions than does $\gamma$-Al$_2$O$_3$. The structural similarity to the spinels and the presence of hydrogen (as H⁺ at tetrahedral sites, as water of hydration or as surface hydroxyl groups) leads to the formulas, HO$_{0.5}$Al$_{0.5}$[Al$_2$O$_4$] and Al[H$_{0.5}$Al$_{1.5}$]O$_4$ for the $\gamma$- and $\eta$-polymorphs, respectively. The square brackets enclose the ions located at octahedral sites. Lewis acid activity of these aluminas originate in the electron deficiency of the aluminum ions at the tetrahedral sites. That these ions are indeed the site of Lewis acidity has been shown by the results of the well-known pyridine adsorption-infra-red spectroscopy test. (Morterra et al, Journal of Catalysis, Vol. 51. pp. 299–313 1978).

Contrastingly, in alpha alumina all the Al³⁺ ions are located at octahedral sites in a hexagonal close packing arrangement of oxide anions. The pyridine adsorption infrared spectroscopy test shows that Lewis acidity does not exist in or on pure alpha alumina (Morterra et al, Journal of Catalysts, Vol. 54 pp. 348–364 1978). Hence pure alpha alumina is not useful for the instant invention.

The nature or strength of the Lewis-acid site, the type of Lewis acid employed and the conditions (i.e. temperature, pressure, contact time and molar ratio of starting materials) of the catalysis have a determinative, but non-obvious effect on the redistribution reactions of silanes. For example, (CH$_3$)$_3$SiCl and SiCl$_4$ redistribute in the presence of AlCl$_3$ at 350° C., 1500 Psig, 0.3 hr. according to the equation illustrated below (see U.S. Pat. No. 2,647,912).

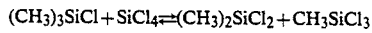

$$(CH_3)_3SiCl + SiCl_4 \rightleftharpoons (CH_3)_2SiCl_2 + CH_3SiCl_3$$

The ratio of dimethyldichlorosilane to methylchlorosilane produced in the latter reaction depends on the contact time the temperature and the pressure in the autoclave. At 400° C. for 10 hr. and 1250 psig. a different reaction pathway is evident as per the following equation see U.S. Pat. No. 2,590,937, Example 11):

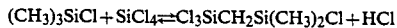

$$(CH_3)_3SiCl + SiCl_4 \rightleftharpoons Cl_3SiCH_2Si(CH_3)_2Cl + HCl$$

However, in the presence of $\gamma$-Al$_2$O$_3$ at 280° C. for 4 hours. The same reagents yielded primarily CH$_3$SiCl$_3$ (Japanese Pat. 1822/1957).

Examples of suitable alumina catalysts which can be used in accordance with the present invention include aluminas having spinel type structures such as $\eta$-Al$_2$O$_3$ and $\gamma$-Al$_2$O$_3$. The hydrated aluminas such as gibbsite, boehmite, and bayerite, however, require calcination to remove water and generate to Lewis acidity. This calcination must be performed under carefully controlled pressure and temperature (heat treatment) conditions to obtain the crystalline Lewis acid-activated aluminas. Calcination procedures are well known to those skilled in the art of preparing or manufacturing activated aluminas (see Maczura et al. Kirk-Othmer Encylopedia of Chemical Technoloqy, 3rd Edition Vol. 2, pp 225–233, John Wiley and Sons, N.Y. 1978). In general, temperatures greater than 850° C. are avoided in order to prevent transformation of the activated aluminas to alpha alumina.

The activated aluminas are items of commerce. As obtained, they already have the spinel type structure demonstrable by its characteristic X-ray diffraction pattern. (See K. Weters and G. Bell, "Oxides and Hydroxides of Aluminum," Technical paper 19, Alcoa Research Labs. 1972). However, it is necessary to heat these commercial materials to remove adsorbed moisture and other volatile contaminants prior to their use as redistribution catalysts. The heat treatment or catalyst activation is done at 400° C.–800° C. for periods of 0.5 to 20 hours. The preferred temperature range is 500° C.–650° C. for periods of 0.5–2 hrs. Activation procedures are well known to those skilled in the use of activated alumina catalysts (B. Linsen, "Physical and Chemical Aspects of Adsorbents and Catalysts." Academic Press, London 1970).

The alumina catalysts of the instant invention must be specifically activated to generate Lewis acid sites. The activation and regeneration procedure of the instant invention differs significantly from that disclosed by the aforementioned U.S. Pat. Nos. 3 346,349 and 3.207,699. The activation and regeneration procedures of these patents actually destroy the acidity of the silica alumina catalyst. Neither patent discloses the desirability of using eta or gamma-alumina. On the contrary, silane-treated rehumidified eta alumina is disclosed in Example 4 of U.S. Pat. No. 3,207,699 as an inferior redistribution catalyst.

Activation of the alumina (heat treatment) can be performed in a separate reactor or in situ in the same reactor used for the redistribution reaction. The latter mode is preferred because any transfer of the activated catalyst carries the risk of surface re-hydration. The spent catalyst remaining after the redistribution reaction can also be regenerated in situ. During activation and regeneration a dry, inert gas such as dried air, nitrogen, argon or helium flows through the catalyst bed as the temperature is raised to the desired temperature. The flow is maintained once this temperature has been reached as well as during the cooling stage. Periods as short as 0.1 hour may be used for activation. However, the preferred time is 0.5–2 hrs. at 500° C.–650° C. The flow rate of the dry, inert gas can cover a broad range, i.e. 0.5–50 lit/min. At the lower limit of this range, it is only necessary to allow the volatile materials released from the hydrated alumina to be swept away. At the upper limit of this range, the maximum gas flow keeps the catalyst contained in the reactor. Alternatively, the regeneration and activation procedure may be performed in vacuo at 400° C.–800° C. or with reactive gases such as HCl or HF. When reactive gases are used it is essential that post-treatment with an inert gas be employed to destroy the Bronsted acid sites formed.

The activated alumina catalyst may be used as a fine powder as granules or as pellets. The larger particle size facilitates the flow of gaseous reactants and products through the fixed catalyst bed. The extruded pellets may contain any of the common binders. e.g. clay, silica, alumina, graphite, etc To prepare an alumina catalyst containing Z5 less than 1% graphite, hereinafter referred to as a "graphite-1 lubricated alumina" catalyst graphite (less than 1%) is mixed with a powdered alumina catalyst. The "graphite-lubricated alumina" catalyst is then pelletized or granularized. The addition of graphite to an alumina catalyst increases its crush strength. Increasing the crush strength of the catalyst increases the ability of the catalyst to maintain its structural integrity and hence prolongs the life of the catalyst.

The catalytic activity of the alumina depends on its crystal structure, pore-size distribution and surface area. These properties in turn are dependent on the precise activation procedure followed The preferred activated aluminas of this invention have median pore sizes in the range of 50 Å–150 Å and surface areas of 100–350 m$^2$/gm. Once the alumina catalyst has been Lewis-acid activated, the mixtures of organohalosilanes are passed through the catalyst bed at temperatures of 200° C.–450° C., preferably 300° C.–350° C. for a maximum contact time (reaction time) of less ten minutes preferably less than five minutes, in order to achieve the same degree of redistribution or better than that achieved by the prior art.

EXPERIMENTAL

The following experimental description illustrates the present invention. In the experimental description the following abbreviations are used:

| Abbreviation | Meaning |
|---|---|
| Ar | phenyl group |
| Catalyst A* | A gamma alumina catalyst in the form of ⅛ in. extrudates, with surface area of 224.6 m$^2$/gm, median pore diameter of 64Å, packing density of 0.68 gm/cm$^3$ and crush strength of 15.6 FPCS, lbs. (Commercially known as Alumina "SA-6173"). |
| Catalyst B* | A gamma alumina catalyst in the form of 1/16 in. extrudates, with surface area of 211.3 m$^2$/gm, median pore diameter of 72Å, packing density of 0.68 gm/cm$^3$ and crush strength of 11.3 FPCS, lbs. (Commercially known as Alumina "SA-6173"). |
| Catalyst C* | A gamma alumina catalyst in the form of ⅛ in. spheres having a surface area of 109 m$^2$/gm and crush strength of 13.0 FPCS, lbs. (Commercially known as Calsicat E-149SC). |
| Catalyst D* | A gamma alumina catalyst in the form of ⅛ in. tablets, having a surface area of 175 m$^2$/gm, median pore size less than 100Å, a density of 0.78 gm/cc, and crush strength of 12.0 FPCS, lbs. (Commercially known as Alumina AL-3438T). |
| Catalyst E* | A gamma alumina catalyst in the form of ⅛ in. spheres with a surface area of 312.55 m$^2$/gm, average pore diameter of 58Å, density of 0.68 m/cc and crush strength of 19.1 FPCS. (Commercially known as Alumina SA-74179). |
| cc | cubic centimeter |
| D | $(CH_3)_2SiCl_2$ |
| DC | $H_2SiCl_2$ |
| DM | $(CH_3)_2SiHCl$ |
| FPCS | Flat plate crush strength, lbs. |
| ft. | foot |
| gm | gram |
| hr. | hour |
| HVS | higher boiling methylchlorosiloxanes, oligomeric and cyclic methylsiloxanes from Rochow Synthesis, generally having boiling points of greater than 100° C. |
| Lights | primarily CH$_3$Cl, butane and pentane, from Rochow Synthesis and generally having boiling points of less than 37° C. |
| M | $(CH_3)_3SiCl$ |
| ml. | milliliters |
| MD | $CH_3SiHCl_2$ |
| Q | $(CH_3)_4Si$ |
| Sec. | seconds |
| SCFH | standard cubic feet per hour |
| T | $CH_3SiCl_3$ |
| TC | $HSiCl_3$ |
| Tet | $SiCl_4$ |

*All catalysts were obtained commercially already having approximately 100% Lewis activated sites thereon, but became partially inactive on storage.

PROCEDURE A: Activation (Heat Treatment) of Alumina Catalysts

In the preferred form of this process, the invention is conducted with activated alumina catalysts having a high proportion of Lewis-acid sites. It should be noted that when purchased all the catalysts utilized in these examples already contained approximately 100% activated Lewis acid sites. However, when said catalysts were handled and exposed to air, reactivation was necessary.

Activation of the alumina can be performed in a separate reactor or in situ in the same reactor (FIG. 1) used for the redistribution reactions. The spent catalyst can also be regenerated in situ. During activation and regeneration a dry, inert gas such as air nitrogen, argon or helium is made to flow through the catalyst bed as the temperature is raised to the desired setting. Flow is maintained after this temperature has been attained as well as during the cooling stage. Periods as short as 0.1 hour may be used for activation. However, the preferred time is 0.5–2 hrs. at 500° C.–650° C. It should be noted once again that activation time is distinguished from the reaction time which is substantially shorter (less than 10 minutes). The flow rate of the dry, inert gas can cover a broad range, 0.5–50 lit/min. At the lower end, it is only necessary that volatile materials released from the hydrated alumina be swept away. The upper limit is the maximum gas flow which still keeps the catalyst contained in the reactor. Alternatively, the dehydration and activation may be performed in vacuo at 400° C.–800° C. or with reactive gases such as HCl or HF. When reactive gases are used it is essential that post-treatment with an inert gas be employed to destroy the Bronsted acid sites formed.

EXAMPLES

All of the following examples utilized activated alumina catalysts and the apparatus outlined in FIG. 1.

The "forecut" or "lower-boiling fraction" mentioned in the Examples, is that fraction of the product from the Rochow synthesis (see U.S. Pat. No. 2,380,99) with a boiling point of less than 40° C. Its principal components and their concentration ranges are typically as follows:

| Compound | Boiling Pt. °C. | Range, Wt % |
|---|---|---|
| Tetramethylsilane | 26.5 | 40–75 |
| Dimethylchlorosilane | 36.0 | 3–25 |
| Methldichlorosilane | 40.7 | 2–9 |
| Monomethylmonochlorosiline | 8.7 | 1–5 |
| Trichlorosilane | 31.8 | 5–10 |
| Methyl Chloride | −24.0 | 5–10 |
| Hydrocarbons | 30–37 | 5–8 |

The hydrocarbons are mostly $C_4$ and $C_5$ paraffins and olefins. The forecut contains no dimethyldichlorosilane and the desired reaction is as follows:

$$(CH_3)_4Si + (CH_3)_2SiCl_2 \rightleftharpoons 2(CH_3)_3SiCl$$

Dimethyldichlorosilane is added to said forecut in a molar amount, which is at least equal to the molar amount of tetramethylsilane. In practice, a slight excess (up to 10%) of dimethyldichlorosilane is used in order to force the equilibrium reaction in favor of $(CH_3)_3SiCl$.

The methyl lights stream, "Lights" shown in the examples, boils below 37° C. It is the product cut between methylchloride and methyldichlorosilane, in the methyls crude stream. After separation, the stream contains the following components:

|  |  | BP (°C.) |
|---|---|---|
| Tetramethylsilane | $Me_4Si$ | 26.5 |
| Dimethylchlorosilane | $Me_2SiHCl$ | 36.0 |
| Trichlorosilane | $HSiCl_3$ | 40.7 |
| Monomethylmonochlorosilane | $MeSiH_2Cl$ | 8.7 |
| Methyl Chloride | MeCl | −24.0 |
| Hydrocarbons: |  |  |
| Iso-butane | Iso-$C_4$ | −11.7 |
| Iso-pentane | Iso-$C_5$ | 28.0 |
| n-pentane | n-$C_5$ | 36.3 |
| Amylene, etc. |  | 30–37 |

The stream contains hydrocarbons in addition to methylchlorosilane monomers and methylchloride. The hydrocarbons are the by-products of methylchloride cracking in the methyl reactors used in the Rochow synthesis.

EXAMPLE 1

Catalyst A was used in this example. The Hastelloy B cylinder reactor had internal dimensions of 3 ft.×¾ inch.

198.5 gm of the Catalyst A was activated by heating for 0.5 hr. at 400° C. (in situ) as per procedure A in dried air. A methylchlorosilane mixture having the composition shown in the first row of Table 1 was made by blending dimethyldichlorosilane with the forecut from the distillation of the crude product obtained from the Rochow Synthesis. The mixture was vaporized at 300° C. and contacted with the activated alumina catalyst at temperatures in the range 200°–40° C. (reaction temperature). The pumping speed was varied to obtain a range of contact times. Samples were taken after 4–5 time constants to ensure that the system had attained steady-state.

Example 1 was used to determine how much conversion to trimethylchlorosilane (M) would be obtained in a temperature range of 200° C.–400° C. an at various flow rates. The reaction began with zero amount (trace) of trimethylchlorosilane (M). At approximately 300° C.–400° C. the maximum amounts of trimethylchlorosilane (M) were obtained, approximately 58.0–68.3%. As the temperature was increased, the conversion of tetramethylsilane (Q) and dimethyldichlorosilane (D) to trimethylchlorosilane (M) also increased. Deactivation of the catalyst bed was evident by the final entries at temperature range of 305° C.–300° C.

TABLE 1

| | | Redistribution of Methylchlorosilanes over Catalyst A at 200° C.–400° C., 0 psig | | | | | | | | |
|---|---|---|---|---|---|---|---|---|---|---|
| Temp. °C. | Liquid Flow rate (ml/min) | % M | % Q | % D | % DM | % MD | % T | % TC | % Lights | % HVS |
| — | 0 | trace | 35.8 | 50.4 | 0.9 | 4.9 | trace | 2.0 | 2.3 | 1.7 |
| 200 | 0.29 | 30.3 | 22.9 | 41.5 | 1.2 | 0.6 | 0.4 | trace | 2.1 | 0.8 |
| 200 | 0.51 | 17.5 | 29.4 | 46.0 | 1.4 | 2.7 | 0.4 | 0.4 | 2.1 | 0.2 |
| 200 | 1.15 | 7.9 | 33.6 | 49.1 | 1.2 | 3.8 | 0.2 | 1.1 | 2.4 | 0.7 |
| 300 | 1.04 | 58.4 | 5.1 | 31.0 | 1.1 | trace | 0.3 | trace | 1.8 | 2.2 |
| 300 | 0.29 | 68.3 | 2.7 | 24.3 | 0.7 | trace | 0.2 | trace | 1.7 | 1.8 |
| 300 | 0.55 | 60.3 | 6.9 | 26.1 | 1.9 | trace | 0.4 | trace | 2.1 | 2.1 |
| 400 | 0.52 | 62.8 | 1.3 | 31.5 | 0.3 | trace | 0.4 | trace | 1.5 | 2.1 |
| 400 | 1.07 | 59.2 | 7.0 | 26.1 | 2.8 | 0.1 | 0.5 | trace | 2.4 | 1.7 |
| 400 | 0.27 | 67.1 | 5.0 | 21.5 | 1.6 | trace | 0.4 | trace | 2.0 | 2.3 |
| 399 | 0.54 | 58.2 | 8.2 | 25.5 | 3.6 | 0.2 | 0.6 | trace | 2.7 | 1.0 |
| 402 | 0.63 | 58.0 | 8.2 | 25.3 | 3.8 | 0.2 | 0.6 | trace | 2.7 | 1.1 |
| 401 | 0.60 | 58.6 | 8.0 | 25.1 | 3.6 | 0.2 | 0.6 | trace | 2.6 | 1.1 |
| 400 | 1.24 | 37.9 | 16.6 | 37.3 | 3.2 | 0.1 | 0.9 | trace | 3.2 | 0.8 |
| 305 | 0.55 | 16.6 | 30.2 | 45.1 | 1.7 | 3.2 | 0.4 | 0.6 | 2.3 | trace |
| 304 | 0.50 | 15.9 | 30.0 | 45.2 | 1.8 | 3.3 | 0.3 | 1.3 | 2.1 | trace |
| 305 | 0.47 | 15.6 | 30.2 | 45.4 | 1.7 | 3.2 | 0.3 | 1.2 | 2.5 | trace |
| 300 | 1.34 | 6.4 | 34.6 | 49.6 | 1.3 | 4.2 | 0.2 | 1.4 | 2.2 | trace |

EXAMPLE 2

Catalyst A was used in Example 2. The catalyst was activated as per Example 1. The feed consisted of a methylchlorosilane mixture having the composition shown in the first row of Table 2. It was made by blending dimethyldichlorosilane with the forecut from the distillation of the crude product obtained from the Rochow synthesis Temperature pressure and liquid flow rates (feed rates) were further varied in order to select optimum operating conditions. The data is shown below in Table 2. Steady-state can be attained within 30 seconds at 400° C., however at 300° C. it requires 120 seconds and at 200° C. about ten minutes. Since pyrolysis of the methylchlorosilanes is expected to be more extensive at 400° C., this experiment was done to determine the optimum temperature range at which the redistribution reaction could be performed. The optimum temperature range for the redistribution reaction ls 300°–400° C. This is illustrated by the fact that the trimethylchlorosilane (M) concentration remained the highest (67.2%–70%) in this temperature range. The principal redistribution reaction is $$(CH_3)_4Si + (CH_3)_2SiCl_2 \rightleftharpoons 2(CH_3)_3SiCl$$

so pressure variations should not affect the position of equilibrium. Nonetheless pressure variations do affect the gas residence time.

TABLE 2

Redistribution of Methylchlorosilanes over ⅛ in. Extrudate at 200° C.-400° C., 0-35 psig

| Temp. °C. | Press. psig. | Liquid Flow rate (ml/min | % M | % Q | % D | % DM | % MD | % T | % TC | % Lights | % HVS |
|---|---|---|---|---|---|---|---|---|---|---|---|
| — | — | — | trace | 38.7 | 51.7 | 1.15 | 4.8 | trace | 1.3 | 2.3 | 0.1 |
| 400 | 35 | 0.29 | 67.2 | 4.8 | 20.8 | 1.4 | trace | 0.3 | trace | 1.8 | 3.5 |
| 400 | 35 | 1.17 | 67.4 | 5.4 | 20.1 | 2.9 | 0.1 | 0.3 | trace | 2.4 | 1.3 |
| 300 | 35 | 1.17 | 68.1 | 3.6 | 20.3 | 3.5 | 0.2 | 0.4 | trace | 2.2 | 1.5 |
| 300 | 35 | 0.29 | 70.0 | 3.9 | 18.1 | 3.3 | 0.1 | 0.2 | trace | 1.8 | 2.4 |
| 200 | 35 | 0.29 | 72.9 | 3.3 | 14.5 | 3.9 | 0.1 | 0.4 | trace | 3.1 | 1.6 |
| 200 | 0 | 1.17 | 30.2 | 21.6 | 39.6 | 1.8 | 2.4 | 0.1 | 1.6 | 1.9 | 0.5 |
| 200 | 0 | 0.29 | 52.1 | 8.6 | 31.8 | 2.3 | 1.3 | 0.2 | 1.2 | 1.7 | 0.6 |
| 300 | 0 | 0.29 | 69.2 | 4.4 | 18.8 | 3.0 | 0.2 | 0.4 | trace | 2.1 | 1.7 |
| 300 | 0 | 1.17 | 56.9 | 11.8 | 24.1 | 2.4 | 1.0 | 0.3 | 0.6 | 2.3 | 0.6 |
| 300 | 10 | 0.58 | 69.8 | 4.8 | 17.9 | 3.3 | 0.2 | 0.4 | trace | 2.5 | 0.9 |
| 400 | 0 | 1.17 | 65.3 | 5.9 | 21.0 | 3.6 | 0.3 | 0.4 | trace | 2.9 | 0.6 |
| 400 | 0 | 0.29 | 65.8 | 5.7 | 21.2 | 2.2 | 0.1 | 0.5 | trace | 2.4 | 2.1 |

EXAMPLE 3

66.6 gm of Catalyst B was activated as described in Example 1. The Hastelloy B cylinder reactor had internal dimensions of 1 ft.×¾ in. The blend of dimethyldichlorosilane and the distillation forecut* had the initial composition shown in the first row of Table 3. The reaction was performed at 400° C. This Example was done to determine the optimum temperature, pressure, and reaction time for the present invention. The optimum temperature range was 300° C.-400° C. and the optimum contact time was approximately 30 seconds. The data indicate that residence times of 32 seconds were sufficient for optimum trimethylchlorosilane (M) formation.

* As previously explained in the introduction to the examples.

EXAMPLE 4

64.2 gm of Catalyst B was charged into a Hastelloy B cylinder reactor having an internal dimensions of 1 ft×¾ in. The catalyst was then activated by heating it to 400° C in dried air as described in Example 1. The liquid methylchlorosilane blend was fed to the catalyst at 33.5 ml/hr continuously for 54.5 hr. At that time the temperature was shut-off and the catalyst was purged with dried nitrogen for 48 hours.

This Example was done to determine when degeneration of the catalyst bed would take place and the effect catalyst regeneration would have on trimethylchlorosilane production. The results (Table 4) show that satisfactory trimethylchlorosilane (M) production was maintained for the initial 54.5 hours. The amount of trimethylchlorosilane (M) production steadily decreased as the catalyst degenerated over a cumulative reaction time of over 50 hours. After catalyst regeneration was obtained with a nitrogen purge, the amount of trimethylchlorosilane (M) produced jumped from 29.8% (before catalyst regeneration) to 34.5%.

TABLE 3

Redistribution of Methylchlorosilanes over Catalyst B at 400° C.

| Cumulative Reaction Time, Hr. | Contact Time (sec) | Press. psig. | % M | % Q | % D | % DM | % MD | % T | % TC | % Lights | % HVS |
|---|---|---|---|---|---|---|---|---|---|---|---|
| 0 | — | — | 0 | 23.2 | 36.5 | 24.9 | 1.1 | — | 8.4 | 5.9 | — |
| 1.25 | 38.7 | 2 | 44.2 | 2.0 | 34.4 | 10.1 | 1.4 | 0.6 | 0.6 | 5.7 | 1.0 |
| 2.25 | 44.4 | 2 | 44.4 | 1.5 | 31.4 | 11.8 | 1.8 | 0.9 | 0.2 | 5.9 | 1.1 |
| 3.5 | 34.5 | 2 | 44.2 | 1.5 | 31.0 | 12.2 | 1.8 | 0.8 | 0.2 | 7.4 | 0.8 |
| 4.5 | 38.2 | 2 | 44.2 | 1.6 | 30.8 | 12.3 | 1.9 | 0.8 | 0.2 | 7.2 | 1.0 |
| 5.5 | 32.0 | 2 | 43.8 | 1.7 | 30.9 | 12.5 | 1.8 | 0.7 | 0.3 | 7.1 | 1.2 |
| 6.0 | 7.4 | 0 | 27.9 | 9.0 | 35.9 | 14.8 | 1.0 | 0.2 | 3.6 | 6.7 | 0.9 |
| 6.3 | 14.7 | 0 | 34.6 | 6.1 | 34.5 | 13.4 | 1.2 | 0.4 | 2.1 | 6.7 | 1.0 |
| 6.5 | 2.0 | 0 | 10.7 | 17.1 | 38.3 | 19.3 | 0.9 | 0.1 | 6.6 | 6.8 | 0.2 |

TABLE 4

Continuous Redistribution of Methylchlorosilanes over Catalyst B at 400° C., 0 psig

| Cumulative Reaction Time, Hr. | % M | % Q | % D | % DM | % MD | % T | % TC | % Lights | % HVS |
|---|---|---|---|---|---|---|---|---|---|
| 0 | — | 39.8 | 49.8 | 1.1 | 4.9 | — | 1.8 | 2.5 | 0.1 |
| 1 | 58.5 | 8.9 | 25.6 | 2.9 | 0.3 | 0.5 | trace | 2.5 | 0.5 |
| 2.5 | 55.9 | 10.2 | 25.4 | 3.6 | 0.5 | 0.6 | trace | 2.7 | 1.0 |
| 4.0 | 43.2 | 16.9 | 32.0 | 2.8 | 1.2 | 0.6 | trace | 2.6 | 0.6 |
| 6.0 | 48.8 | 13.9 | 28.8 | 3.2 | 0.9 | 0.6 | trace | 2.8 | 0.9 |
| 8.0 | 42.3 | 17.1 | 31.8 | 3.1 | 1.4 | 0.6 | 0.2 | 2.7 | 0.7 |
| 10.0 | 39.1 | 18.9 | 33.6 | 2.8 | 1.7 | 0.5 | 0.3 | 1.9 | 0.6 |
| 12.0 | 41.7 | 17.8 | 31.7 | 2.5 | 1.2 | 0.9 | 0.2 | 2.5 | 1.5 |

TABLE 4-continued

Continuous Redistribution of Methylchlorosilanes over Catalyst B at 400° C., 0 psig

| Cumulative Reaction Time, Hr. | % M | % Q | % D | % DM | % MD | % T | % TC | % Lights | % HVS |
|---|---|---|---|---|---|---|---|---|---|
| 14.0 | 36.7 | 20.4 | 34.7 | 2.7 | 1.8 | 0.5 | 0.1 | 2.4 | 1.1 |
| 16.0 | 33.9 | 22.0 | 36.3 | 2.3 | 1.8 | 0.5 | trace | 2.3 | 0.8 |
| 19.0 | 36.6 | 20.2 | 34.7 | 2.8 | 1.9 | 0.5 | 0.1 | 2.5 | 0.6 |
| 21.0 | 35.2 | 20.9 | 35.4 | 2.6 | 2.0 | 0.5 | 0.2 | 2.4 | 0.8 |
| 23.5 | 43.5 | 17.3 | 31.3 | 2.9 | 1.4 | 0.6 | 0.2 | 2.4 | 0.4 |
| 26.5 | 41.2 | 18.4 | 32.7 | 3.0 | 1.4 | 0.6 | 0.1 | 2.5 | 0.3 |
| 29.5 | 35.9 | 20.9 | 35.1 | 2.8 | 1.9 | 0.6 | 0.2 | 2.4 | 0.2 |
| 31.5 | 33.4 | 21.8 | 36.5 | 2.7 | 2.2 | 0.5 | 0.4 | 2.3 | 0.2 |
| 34.5 | 31.9 | 22.9 | 36.6 | 2.6 | 2.3 | 0.5 | 0.5 | 2.4 | 0.3 |
| 37.5 | 32.4 | 21.5 | 39.0 | 1.7 | 1.9 | 0.5 | 0.2 | 2.1 | 0.4 |
| 40.5 | 31.1 | 23.5 | 37.6 | 2.0 | 2.2 | 0.5 | 0.4 | 2.3 | 0.3 |
| 45.5 | 29.8 | 24.0 | 38.3 | 2.2 | 2.3 | 0.5 | 0.4 | 2.3 | 0.2 |
| 48.5 | 35.9 | 21.1 | 34.9 | 2.6 | 1.9 | 0.5 | 0.4 | 2.3 | 0.2 |
| 51.5 | 32.8 | 22.3 | 36.4 | 2.8 | 2.1 | 0.6 | 0.4 | 2.4 | 0.2 |
| 54.5 | 29.8 | 23.9 | 37.8 | 2.4 | 2.4 | 0.5 | 0.6 | 2.4 | 0.2 |
| REACTOR SHUT DOWN AND PURGED WITH DRIED N₂ FOR 48 HRS. | | | | | | | | | |
| 56.5 | 34.5 | 19.3 | 38.6 | 2.2 | 2.1 | 0.4 | 0.6 | 1.8 | 0.5 |
| 57.5 | 31.4 | 22.6 | 37.3 | 2.5 | 2.5 | 0.5 | 0.8 | 2.2 | 0.2 |
| 59.5 | 26.8 | 24.5 | 39.6 | 2.4 | 2.8 | 0.8 | 0.9 | 2.2 | 0.3 |
| 61.5 | 23.9 | 26.4 | 40.4 | 2.3 | 3.0 | 0.4 | 1.1 | 2.3 | 0.2 |

EXAMPLE 5

62.8 gm of Catalyst B was charged in a Hastelloy B cylinder reactor having internal dimensions of 1 ft. × ¾ in. The feed consisted of a methylchlorosilane mixture having the composition shown in the first row of Table 5. It was made by blending dimethyldichlorosilane with the forecut from the distillation of the crude product obtained from the Rochow Synthesis. The feed flow rate of the reaction mixture was 28.3 ml liquid/hr and the reactor temperature was 400° C. The reaction was performed for a total of 24 hours over a five-day period. At the end of each day's run the catalyst was purged overnight with dried air, dried nitrogen, dried HCl or dried H₂ as shown in Table 5.

This Example was done in order to determine the best regeneration procedure. The best regeneration results were achieved utilizing a nitrogen purge. This is evidenced by the fact that after regeneration with nitrogen after 16.75 hrs., the trimethylchlorosilane (M) concentration increased from approximately 15.3% to 37.4%.

Presumably, the gases regenerate the catalyst by clearing the micropores which have become blocked during the reaction. When silyl residues left on the catalyst surface and in the pores are decomposed at the regeneration temperature (400° C.), Bronsted acid sites result. These sites must be destroyed by thermal treatment to restore Lewis acidity and the desired catalytic activity.

TABLE 5

Redistribution of Methylchlorosilanes over Catalyst B at 400° C. with Intermittent Regeneration

| Cumulative Reaction Time, Hr. | % M | % Q | % D | % MD | % DM | % T | % TC | % Lights | % HVS |
|---|---|---|---|---|---|---|---|---|---|
| 0 | — | 35.8 | 51.6 | 5.0 | 0.4 | trace | 2.5 | 4.4 | trace |
| 0.5 | 55.0 | 5.9 | 29.3 | 0.6 | 2.3 | 0.9 | 0.2 | 3.4 | 2.4 |
| 2.75 | 57.4 | 6.8 | 25.6 | 0.5 | 3.6 | 0.9 | trace | 4.5 | 0.7 |
| 5.0 | 57.4 | 7.1 | 25.2 | 0.5 | 3.8 | 0.9 | 0.1 | 4.4 | 0.6 |
| REGENERATE WITH DRIED AIR OVERNIGHT | | | | | | | | | |
| 6.5 | 42.8 | 12.3 | 35.2 | 0.7 | 3.1 | 0.9 | 0.1 | 4.2 | 0.7 |
| 8 | 37.2 | 15.9 | 36.8 | 1.2 | 3.0 | 0.9 | 0.1 | 4.0 | 0.9 |
| 9 | 26.7 | 21.5 | 41.0 | 2.0 | 2.6 | 1.3 | 0.3 | 3.9 | 0.7 |
| 12.0 | 20.4 | 24.6 | 43.9 | 2.5 | 2.1 | 1.3 | 0.6 | 4.0 | 0.6 |
| REGENERATE WITH DRIED AIR OVERNIGHT | | | | | | | | | |
| 13.0 | 30.0 | 18.7 | 42.2 | 1.4 | 2.2 | 1.0 | 0.1 | 3.7 | 0.7 |
| 14.0 | 19.7 | 24.7 | 45.1 | 2.3 | 2.0 | 1.2 | 0.4 | 4.0 | 0.6 |
| 16.75 | 15.3 | 28.4 | 45.1 | 2.8 | 1.7 | 1.4 | 0.6 | 4.1 | 0.7 |
| HCl @ 0.5 SCFH for 0.5 hr, N₂ for 0.5 hr followed by DRIED AIR OVERNIGHT | | | | | | | | | |
| 17.25 | 37.4 | 15.0 | 38.5 | 1.8 | 1.8 | 0.9 | 0.6 | 3.5 | 0.3 |
| 18.75 | 34.0 | 17.9 | 38.4 | 1.8 | 2.1 | 0.9 | 0.4 | 4.1 | 0.4 |
| 19.50 | 20.1 | 25.5 | 43.8 | 2.6 | 1.7 | 1.2 | 0.7 | 3.9 | 0.3 |
| 21.50 | 15.2 | 28.1 | 45.5 | 3.1 | 1.5 | 1.4 | 1.0 | 3.9 | 0.3 |
| 23.50 | 13.1 | 29.3 | 46.5 | 3.3 | 1.3 | 1.3 | 1.0 | 3.9 | 0.3 |
| HCl @ 0.75 SCFH for 2.5 hr, N₂ for 0.5 hr followed by DRIED AIR OVERNIGHT | | | | | | | | | |
| 24 | 17.4 | 22.6 | 50.7 | 2.9 | 1.1 | 0.9 | 0.9 | 3.1 | 0.3 |

EXAMPLE 6

63.2 gm of Catalyst B was used in the reactor as outlined in Example 1. The feed consisted of a methylchlorosilane mixture having the composition shown in the first row of Table 6. It was made by blending dimethyldichlorosilane with the forecut from the distillation of the crude product from the Rochow Synthesis. The liquid feed rate of the reactor was 31.88 ml/hr. The reactor temperature was 400° C. The nitrogen flow was sustained at this temperature for 16-18 hr. periods between successive runs A thru G as indicated by the straight lines between runs in Table 6.

This Example illustrates that intermittent treatment with dried nitrogen restores and/or maintains catalytic activity at a desirable level of trimethylchlorosilane (M) production. The results achieved with the nitrogen purge are particularly pronounced in Runs D through G. Once regeneration began with nitrogen after 15.39 hrs. (end of Run C), the trimethylchlorosilane (M) concentration increased from 32.8% to 47.1%. After regeneration at 22.67 hours, the trimethylchlorosilane (M) concentration increased from 32.6% to 40.6%. After regeneration at 34.68 hours. the trimethylchlorosilane (M) concentration increased from 29.7% to 45.8%.

treatment of the gamma-alumina catalyst is suitable as an activation procedure and also as a regeneration method. Hydrofluorination of alumina apparently increases the population of Lewis acid sites. Table 7 shows that the catalyst performance was comparable to that of Example 3. The amount of trimethylchlorosilane (M) produced, 44.2%-43.5% after 3 hrs. was certainly comparable to !hat produced in Example 3, which utilized a catalyst which had been activated utilizing a dry inert gas.

EXAMPLE 8

213.7 gm of Catalyst C was charged into a Hastelloy B cylinder reactor having the dimensions outlined in Example 1. The catalyst was activated by heating it to 400° C. in a stream of dried air (4.89 lit/min). The catalyst was evaluated at 200° C. and at 400° C. in a manner analogous to that described in Example 1. The reaction mixture had the composition shown in the first row of Table 8 and was prepared as illustrated in the previous examples.

Table 8 shows that this lower surface area catalyst also performed satisfactorily at 400° C., but longer residence times were required than those shown in Examples 1 through 3. Since the gamma-alumina spheres (Catalyst C) utilized in this example bad smaller surface areas than the extrudates (Catalyst B) utilized in Example 3, longer contact times were needed to achieve good results.

TABLE 6

Redistribution of Methylchlorosilanes over Catalyst B at 400° C. with Intermittent N$_2$ Regeneration of the Catalyst

| | Cumulative Reaction Time (hr) | % M | % Q | % D | % MD | % TC | % DM | % T | % Lights | % HVS |
|---|---|---|---|---|---|---|---|---|---|---|
| Run A | 0 | — | 34.5 | 53.3 | 5.1 | 2.6 | 0.4 | — | 4.1 | tr |
| | 1 | 57.4 | 6.6 | 26.9 | 0.4 | 0.1 | 3.4 | 0.7 | 4.0 | 0.5 |
| | 1.83 | 57.1 | 6.4 | 26.8 | 0.5 | 0.1 | 3.8 | 0.8 | 4.0 | 0.5 |
| | 2.83 | 56.6 | 6.5 | 27.0 | 0.6 | 0.1 | 3.9 | 0.9 | 4.0 | 0.4 |
| Run B | 3.41 | 55.4 | 7.0 | 27.4 | 0.6 | 0.1 | 4.2 | 0.9 | 4.0 | 0.4 |
| | 5.58 | 54.6 | 7.4 | 27.6 | 0.7 | 0.1 | 4.2 | 0.9 | 3.9 | 0.4 |
| | 7.25 | 55.0 | 7.3 | 27.4 | 0.7 | 0.1 | 4.1 | 0.9 | 4.0 | 0.4 |
| Run C | 11.92 | 44.0 | 12.5 | 33.7 | 1.2 | 0.2 | 3.4 | 0.8 | 3.5 | 0.4 |
| | 13.17 | 46.2 | 11.6 | 31.9 | 1.1 | 0.1 | 3.9 | 1.0 | 3.7 | 0.4 |
| | 15.39 | 32.8 | 17.8 | 39.3 | 2.3 | 0.5 | 2.9 | 0.9 | 3.6 | 0.2 |
| Run D | 16.92 | 47.1 | 10.9 | 31.6 | 0.8 | tr | 3.7 | 1.0 | 3.6 | 1.3 |
| | 18.54 | 30.0 | 18.7 | 40.6 | 2.1 | 0.4 | 2.9 | 0.9 | 3.5 | 0.8 |
| | 19.76 | 50.1 | 9.1 | 31.5 | 0.9 | 0.1 | 3.7 | 0.9 | 3.3 | 0.4 |
| | 21.09 | 35.1 | 17.4 | 37.0 | 1.8 | 0.3 | 3.4 | 1.0 | 3.5 | 0.3 |
| | 22.67 | 32.6 | 18.5 | 38.3 | 2.0 | 0.3 | 3.2 | 1.1 | 3.7 | 0.3 |
| Run E | 23.26 | 40.6 | 13.1 | 36.6 | 1.6 | 0.3 | 3.3 | 0.9 | 3.2 | 0.2 |
| | 24.26 | 31.0 | 19.5 | 38.7 | 2.2 | 0.4 | 3.2 | 1.0 | 3.7 | 0.2 |
| | 28.17 | 27.1 | 21.1 | 41.2 | 2.5 | 0.5 | 2.8 | 0.9 | 3.3 | 0.2 |
| | 29.26 | 26.9 | 21.6 | 40.7 | 2.6 | 0.5 | 2.8 | 0.9 | 3.3 | 0.1 |
| Run F | 30.01 | 31.5 | 19.1 | 39.1 | 2.2 | 0.3 | 2.9 | 0.8 | 3.6 | 0.4 |
| | 32.01 | 30.9 | 20.0 | 38.3 | 2.2 | 0.4 | 3.2 | 0.9 | 3.8 | 0.2 |
| | 33.20 | 33.7 | 17.9 | 37.5 | 1.9 | 0.3 | 3.4 | 1.0 | 3.7 | 0.6 |
| | 34.68 | 29.7 | 19.6 | 40.0 | 2.3 | 0.4 | 3.1 | 1.0 | 3.6 | 0.3 |
| Run G | 36.26 | 45.8 | 12.8 | 31.1 | 0.9 | 0.1 | 4.0 | 0.9 | 3.9 | 0.5 |
| | 37.18 | 30.3 | 20.0 | 38.3 | 2.1 | 0.3 | 3.4 | 1.1 | 3.9 | 0.6 |
| | 38.43 | 33.9 | 19.1 | 35.1 | 1.8 | 0.2 | 3.8 | 1.2 | 4.1 | 0.8 |
| | 38.93 | 26.9 | 21.7 | 39.5 | 2.4 | 0.4 | 3.1 | 1.2 | 4.0 | 0.8 |

EXAMPLE 7

60.1 gm of Catalyst B was rinsed with a 2% HF aqueous solution (activation procedure) and then dried in a vacuum over at 500° C. for 4 hours. The dried catalyst was placed in a Hastelloy B cylinder reactor having internal dimensions of 1 ft × ¾ in. The catalyst was then heated to 400° C. for reaction with the reaction mixture of methylchlorosilanes having the composition shown in the first row of Table 7. Said reaction mixture was made by blending with dimethyldichlorosilane and the forecut from the Rochow Synthesis as illustrated in the previous examples. This example illustrates that HF

TABLE 7

Redistribution of Methylchlorosilanes over HF treated Catalyst B at 400° C.

| Time, Hr. | Contact Time, (sec) | % M | % Q | % D | % DM | % MD | % T | % TC | % Lights | % HVS |
|---|---|---|---|---|---|---|---|---|---|---|
| 0 | 0 | trace | 19.4 | 43.4 | 24.4 | 1.2 | trace | 7.9 | 3.2 | 0.1 |
| 1 | 66.5 | 44.2 | 3.7 | 31.6 | 11.6 | 1.3 | 0.8 | 0.4 | 2.7 | 3.5 |
| 2 | 33.9 | 43.5 | 4.2 | 29.4 | 13.0 | 1.6 | 0.8 | 0.2· | 3.5 | 3.2 |

TABLE 7-continued

Redistribution of Methylchlorosilanes over HF treated Catalyst B at 400° C.

| Time, Hr. | Contact Time, (sec) | % M | % Q | % D | % DM | % MD | % T | % TC | % Lights | % HVS |
|---|---|---|---|---|---|---|---|---|---|---|
| 3 | 36.8 | 43.5 | 4.0 | 29.3 | 13.0 | 1.8 | 0.9 | 0.2 | 3.9 | 2.9 |

TABLE 8

Redistribution of Methylchlorosilanes over Catalyst C between 200° C.–400° C.

| Temp °C. | Contact Time, (sec) | % M | % Q | % D | % DM | % MD | % T | % TC | % Lights | % HVS |
|---|---|---|---|---|---|---|---|---|---|---|
|  | 0 | 0 | 39.5 | 52.7 | 0.9 | 4.4 | trace | 0.2 | 2.3 | — |
| 200 | 96.9 | 3.9 | 35.6 | 51.6 | 0.6 | 4.7 | 0.4 | 0.1 | 3.1 | — |
| 200 | 23.6 | 3.7 | 35.8 | 51.7 | 0.5 | 4.4 | 0.4 | 0.1 | 3.4 | — |
| 400 | 63.7 | 39.5 | 19.0 | 34.5 | 3.0 | 0.6 | 0.9 | — | 2.4 | 0.1 |
| 400 | 71.6 | 38.7 | 19.1 | 35.0 | 3.3 | 0.6 | 0.9 | — | 2.4 | — |
| 400 | 72.5 | 37.5 | 18.8 | 36.4 | 3.4 | 0.6 | 0.9 | — | 2.4 | — |
| 400 | 90.8 | 37.4 | 18.5 | 36.7 | 3.5 | 0.6 | 0.9 | 0.1 | 2.3 | — |

EXAMPLE 9

The addition of less than 1% graphite to a gamma-alumina catalyst increases the crush strength and handling ease of these catalysts. 80.3 gm of Catalyst D were prepared as described in Example 3. Evaluation was done at 400° C. using a methylchlorosilane blend with the composition shown in the first row of Table 9. The gas residence time was 22 seconds.

This catalyst affords satisfactory production of trimethylchlorosilane (M) and performs as well as those catalysts evaluated in Examples 1 through 3. Table 9 shows the redistribution of Methylchlorosilanes over Graphite-Lubricated Alumina at 400° C.

EXAMPLE 10

The disproportionation of $(CH_3)_2SiHCl$ was studied at 400° C. over Catalyst B. The catalyst was activated by heating it to 400° C in dried air (4.89 lit/min) for 0.5 hr prior to the onset of the reaction. 66.6 gm Catalyst B was used and the reactor was as the utilized in Example 1. The reaction mixture feed rates (liquid flow, ml/min) were varied to obtain different gas residence times. The reaction scheme can be illustrated as follows:

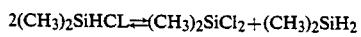

The data indicates that dimethylchlorosilane (DM) is converted primarily into dimethyldichlorosilane (D) and trimethylchlorosilane (M). Both $CH_3SiH_2Cl$ and $(CH_3)_2SiH_2$ were found in the Lights (i.e. most volatile fraction) by gas chromatography and mass spectroscopy analysis. The results are illustrated in Table 1. This example illustrates that the activated alumina catalysts of this invention rearrange H and Cl groups as well as $CH_3$ and Cl.

TABLE 9

Redistribution of Methylchlorosilanes over Graphite-Lubricated Catalyst D at 400° C.

| Cumulative Reaction Time, hr. | % M | % Q | % D | % DM | % MD | % T | % TC | % Lights | % HVS |
|---|---|---|---|---|---|---|---|---|---|
| 0 | — | 34.5 | 53.3 | 0.4 | 5.1 | — | 2.6 | 4.1 | — |
| 1 | 44.4 | 11.9 | 34.5 | 2.4 | 1.0 | 0.9 | 0.2 | 3.7 | 1.0 |
| 2 | 48.0 | 10.0 | 33.7 | 1.7 | 0.9 | 0.7 | 0.2 | 3.8 | 1.0 |
| 2.67 | 51.5 | 8.8 | 30.8 | 3.2 | 0.6 | 1.0 | — | 3.8 | 0.7 |
| 3.50 | 52.3 | 8.6 | 29.2 | 3.5 | 0.5 | 0.9 | — | 3.9 | 1.1 |
| 4.25 | 52.8 | 8.2 | 29.0 | 3.6 | 0.6 | 0.9 | — | 3.9 | 1.0 |

TABLE 10

Redistribution of $Me_2SiHCl$ over Catalyst B at 400° C.

| Liquid Flow ml/min | % M | % Q | % D | % DM | % MD | % T | % Lights | % HVS |
|---|---|---|---|---|---|---|---|---|
| 0 | 0.7 | — | 0.4 | 97.2 | 0.8 | — | 0.1 | 0.8 |
| 0.23 | 21.2 | 0.3 | 32.0 | 35.9 | 3.2 | 0.4 | 5.8 | 1.2 |
| 0.34 | 13.5 | 0.2 | 29.3 | 45.9 | 2.1 | 0.2 | 7.8 | 1.0 |
| 0.70 | 5.5 | 0.1 | 26.7 | 53.6 | 1.0 | 0.1 | 11.7 | 1.3 |
| 1.40 | 2.2 | 0.1 | 20.6 | 64.7 | 0.9 | — | 10.4 | 1.1 |

EXAMPLE 11

The same (unregenerated) catalyst bed (Catalyst B) used for Example 3 was used to redistribute a methylchlorosilane mixture containing 65.9 wt % $SiCl_4$(Tet) and 34.1 wt % $(CH_3)_4Si$ (Q) at 400° C. The liquid feed rate was 12 ml/hr. Analysis of the two samples collected (Table 11) showed 14.0% and 7.0% trimethylchlorosilane (M), respectively. The reaction scheme can be illustrated by the following equation:

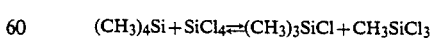

Tetramethylsilane (Q) is present in the lower boiling fraction of the Rochow synthesis. Tetrachlorosilane (Tet) is available from the trichlorosilane direct process. This example was performed to determine what useful compounds could be produced from the waste products. Even at a slow feed rate, not very much conversion occurred.

EXAMPLE 12

A mixture containing 68.3% CH$_3$SiCl$_3$ and 31.3% (CH$_3$)$_4$Si was redistributed on the same catalyst bed used in Example 11 (Catalyst B). Reaction temperature was 400° C. The samples collected contained about 16–17% trimethylchlorosilane. The reaction scheme can be illustrated by the following equation:

$$CH_3SiCl_3 + (CH_3)_4Si \rightleftharpoons (CH_3)_3SiCl + (CH_3)_2SiCl_2$$

methyltrichlorsilane (T) is a byproduct and tetramethylsilane (Q) is present in the forecut lower boiling fraction of the Rochow synthesis. The results are illustrated in Table 12. Even at a residence time of 183.9 sec. very little trimethylchlorosilane (M) is produced.

TABLE 11

Redistribution of Tetramethylsilane and Tetrachlorosilane over Catalyst B at 400° C.

| Cumulative Reaction Time, Hr | % M | % Tet | % Q | % D | % T | % HVS |
|---|---|---|---|---|---|---|
| 0 | — | 67.6 | 32.2 | 0.2 | — | — |
| 0.67 | 14.0 | 67.8 | 15.7 | 2.0 | 0.1 | 0.4 |
| 3.5 | 7.0 | 62.5 | 28.7 | 1.1 | 0.3 | 0.4 |

TABLE 12

Redistribution of Methyltrichlorosilane and Tetramethylsilane over Catalyst B at 400° C.

| Contact Time (sec) | % M | % Q | % D | % T | % Lights | % HVS |
|---|---|---|---|---|---|---|
|  | — | 31.1 | — | 68.3 | 0.1 | 0.4 |
| 67.9 | 15.9 | 16.2 | 2.0 | 64.7 | 0.1 | 1.0 |
| 183.9 | 16.7 | 21.5 | 2.2 | 59.1 | — | 0.5 |

EXAMPLE 13

Another (CH$_3$)$_4$Si - CH$_3$SiCl$_3$ mixture (composition shown in the first row of Table 13) was studied at 400° C. This time the catalyst was 65.3 gm of Catalyst E activated in situ as described in Example 3. The contact time was 40 seconds. The content of trimethylchlorosilane (M) in the samples analyzed is shown in Table 13. This example is a repeat of the experiment performed in Example 12, however a new catalyst bed with a high surface area was utilized. This experiment was performed to determine if the contact time could be shortened utilizing the new catalyst bed with improved results. The results show improvement over the contact times shown in Example 12.

EXAMPLE 14

The unregenerated catalyst bed for Example 13 (Catalyst E) was used to redistribute a 63.4 wt % (CH$_3$)$_2$SiCl$_2$- 36.5 wt % (CH$_3$)$_4$Si mixture at 400° C. and contact time of 42.4 seconds. Trimethylchlorosilane (M) was the major reaction product as illustrated in Table 14. The reaction scheme of this example can be illustrated as follows:

$$(CH_3)_2SiCl_2 + (CH_3)_4Si \rightleftharpoons 2(CH_3)_3SiCl$$

This example was done to determine how well the catalyst bed would operate with pure components. There was a significant improvement in trimethylchlorosilane (M) production over that shown in Example 13. The data shows that the molar amount of (CH$_3$)$_3$SiCl formed is approximately twice the molar amount of (CH$_3$)$_4$Si used as required by the stoichiometry of the reaction.

TABLE 13

Redistribution of Methyltrichlorosilane and Tetramethylsilane over Catalyst E at 400° C.

| Cumulative Reaction Time, hr | % M | % Q | % D | % T | % Lights | % HVS |
|---|---|---|---|---|---|---|
| | — | 47.6 | — | 50.8 | — | 0.5 |
| 0.5 | 39.1 | 21.7 | 3.1 | 30.4 | 0.1 | 5.5 |
| 1.25 | 30.8 | 32.3 | 2.7 | 32.7 | 0.2 | 1.3 |
| 2.0 | 24.3 | 38.4 | 2.6 | 33.5 | 0.2 | 0.9 |

TABLE 14

Redistribution of Dimethyldichlorosilane and Tetramethylsilane over Catalyst E at 400° C.

| Cumulative Reaction Time, hr | % M | % Q | % D | % T | % Lights | % HVS |
|---|---|---|---|---|---|---|
| 0 | — | 36.5 | 63.4 | 0.1 | 0.1 | 1.0 |
| 0.75 | 43.4 | 13.3 | 39.6 | 0.2 | — | 3.6 |
| 1.75 | 54.9 | 13.4 | 30.4 | 0.1 | — | 1.2 |
| 2.75 | 49.3 | 18.2 | 31.6 | 0.1 | 0.1 | 0.7 |

EXAMPLE 15

CH$_3$SiHCl$_2$ was disproportionated at 400° C. over the same catalyst bed previously used for Examples 13 and 14 (Catalyst E). The major product was CH$_3$SiCl$_3$, as illustrated in Table 15. The reaction scheme of this example can be illustrated by the following:

$$2CH_3SiHCl_2 \rightleftharpoons CH_3SiCl_3 + CH_3SiH_2Cl$$

The data of Table 15 illustrate that the activated alumina catalysts of this invention rearranqe H and Cl groups as well as CH$_3$ and Cl groups. This example further illustrates that the Lewis acid catalysts of this invention behave in a different and non-obvious way from the modified silica alumina catalysts of U.S. Pat. No. 3,346,349.

EXAMPLE 16

The mixture for redistribution contained 54.8 wt % CH$_3$SiCl$_3$ and 43.4 wt % H$_2$SiCl$_2$. Catalyst B was heated as described in Example 3. No trimethylchlorosilane (M) was detected. Trichlorosilane (TC) was the principal reaction product. The reaction scheme of this example can be illustrated by the following:

$$H_2SiCl_2 + CH_3SiCl_3 \rightleftharpoons HSiCl_3 + CH_3HSiCl_2$$

The data in Table 16 as well as that of Examples 10 and 15 illustrate that the activated alumina catalysts of this invention rearrange H and Cl groups as well as CH$_3$ and Cl.

TABLE 15

Disproportionation of CH$_3$SiHCl$_2$ over Catalyst E at 400° C.

| Cumulative Reaction Time, Hr. | % M | % Q | % D | % MD | % DM | % T | % TC | % Lights | % HVS |
|---|---|---|---|---|---|---|---|---|---|
| | — | — | 99.0 | 0.3 | — | — | — | 0.1 | 0.6 |
| 1 | 0.2 | 4.1 | 4.2 | 66.1 | 0.7 | 20.7 | 0.7 | 0.2 | 3.1 |
| 1.5 | 0.1 | 6.0 | 4.1 | 61.9 | 0.8 | 23.8 | — | 1.0 | 2.3 |

TABLE 15-continued

Disproportionation of $CH_3SiHCl_2$ over Catalyst E at 400° C.

| Cumulative Reaction Time, Hr. | % M | % Q | % D | % MD | % DM | % T | % TC | % Lights | % HVS |
|---|---|---|---|---|---|---|---|---|---|
| 2.0 | 0.1 | 7.2 | 4.3 | 57.5 | 1.0 | 26.3 | 0.1 | 0.4 | 2.1 |

TABLE 16

Redistribution of Methyltrichlorosilane and $H_2SiCl_2$ over Catalyst B at 400° C.

| Contact Time (sec) | % TC | % DC | % T | % DM | % MD | % TET | % D | % Lights | % HVS |
|---|---|---|---|---|---|---|---|---|---|
|  |  | 1.6 | 43.4 | 54.8 | — | — | 0.1 | — | 0.1 | — |
| 62.7 | 40.4 | 7.4 | 37.4 | 0.3 | 6.5 | 6.8 | 0.6 | — | 0.6 |
| 84.9 | 42.0 | 9.3 | 32.6 | 0.8 | 6.5 | 7.6 | 0.6 | — | 0.6 |
| 92.8 | 42.3 | 8.0 | 31.5 | 0.7 | 6.2 | 10.1 | 0.6 | — | 0.6 |
| 21.2 | 35.0 | 13.4 | 40.9 | 0.9 | 5.2 | 4.2 | — | — | 0.4 |
| 7.8 | 24.4 | 25.0 | 44.1 | 2.1 | 2.8 | 1.2 | — | — | 0.4 |

We claim:

1. A method for redistributing the halogen atom of a halosilane and at least one member selected from the group consisting of the hydrocarbyl group of a hydrocarbylsilane and the hydrogen atom of a hydrosilane which method comprises contacting a mixture of the halosilane, hydrocarbylsilane and/or the hydrosilane, with a heat treated crystalline gamma alumina or eta alumina catalyst at 200° C.–450° C. for a maximum contact time of ten minutes, said heat treated catalyst having been activated at 400° C.–500° C. and regenerated by a process comprising heating the catalyst with a 2% aqueous hydrogen fluoride solution before activation.

2. A method of catalytically redistributing the halogen atom of a halosilane, and at least the hydrocarbyl group of a hydrocarbylsilane or the hydrogen atom of a hydrosilane wherein the silanes being redistributed are present as a mixture comprising two or more distinct halosilane, hydrocarbylsilanes and/or hydrosilanes having the formulas:

$$R_nSiX_{4-n} \text{ and/or } R_mSiHX_{3-m}$$

wherein R is an alkyl group having from 1 to 5 carbon atoms, or an phenyl group, X is a halogen, $n \leq 4$, and $m \leq 3$, which method comprises contacting the mixture of silanes with a heat treated cyrstalline gamma alumina or eta alumina catalyst at 200° C.–450° C. for a maximum contact time of ten minutes, said heat treated catalyst having been activated at 400° C.–500° C. and having been regenerated by a process comprising treating the catalyst with a 2% aqueous hydrogen flouride solution before activation.

3. A method of catalystically redistributing the halogen, the hydrogen, the alkyl groups and/or phenyl groups of a single silane represented by the formula:

$$R_nSiX_{4-n}$$

wherein R is a hydrogen, an phenyl group, or an alkyl group containing from 1 to 5 carbon atoms, X is a halogen, and n has a value from 1 to 3 inclusive which method comprises contacting silane with a heat treated crystalline gamma alumina or eta alumina catalyst at 200° C.–450° C. for a maximum contact time of ten minutes, said heat treated catalysts having been activated at 400° C.–500° C. and having been regenerated by a process comprising treating the catalyst with a 2% aqueous hydrogen fluoride solution before activation.

* * * * *